(12) United States Patent
Da et al.

(10) Patent No.: US 6,932,024 B2
(45) Date of Patent: Aug. 23, 2005

(54) COMPACT PEDIGREES SHOWING HERITABLE TRAITS FOR MANY INDIVIDUALS

(75) Inventors: Yang Da, Maplewood, MN (US); John R. Garbe, Roseville, MN (US)

(73) Assignee: Cargill, Incorporated, Wayzata, MN (US)

( * ) Notice: Subject to any disclaimer, the term of this patent is extended or adjusted under 35 U.S.C. 154(b) by 77 days.

(21) Appl. No.: 10/339,865

(22) Filed: Jan. 9, 2003

(65) Prior Publication Data

US 2004/0134440 A1 Jul. 15, 2004

(51) Int. Cl.[7] .......................... A01K 29/00; G06F 7/00
(52) U.S. Cl. ................................. 119/174; 707/104.1
(58) Field of Search ..................... 119/174; 707/104.1

(56) References Cited

U.S. PATENT DOCUMENTS

| | | | | |
|---|---|---|---|---|
| 4,201,386 A | * | 5/1980 | Seale et al. | 273/236 |
| 5,407,821 A | * | 4/1995 | Breakefield et al. | 435/6 |
| 6,183,258 B1 | * | 2/2001 | Cobb et al. | 434/154 |
| 6,283,065 B1 | * | 9/2001 | Shorrock et al. | 119/863 |
| 6,287,254 B1 | * | 9/2001 | Dodds | 600/300 |
| 6,373,488 B1 | * | 4/2002 | Gasper et al. | 345/427 |
| 6,416,325 B2 | * | 7/2002 | Gross | 434/154 |
| 6,537,213 B2 | * | 3/2003 | Dodds | 600/300 |
| 6,570,567 B1 | * | 5/2003 | Eaton | 345/428 |

OTHER PUBLICATIONS

"Lineage 1.0—Pedigree Visualization and Analysis Software", http://www.ansci.cornell.edu/lineage/, Animal Science at Cornell University, Screen shots—http://www.ansci.cornell.edu/lineage/screens.html.

"Pedigree Visualizer", http://sdmc.lit.org.sg/kleisli/demos/pedigree/, Web–based program.

* cited by examiner

Primary Examiner—Teri P. Luu
Assistant Examiner—Bret Hayes
(74) Attorney, Agent, or Firm—Schwegman, Lundberg, Woessner & Kluth, P.A.

(57) ABSTRACT

Large, complex pedigrees of animals and plants group individuals for improved visualization. A computer transforms data from each mating to display nodes having separate symbols only for groups of offspring having common sex and/or traits. Pedigrees can include complex breeding structures. Input parameters select particular individuals, grouping, and formatting, including visual properties such as colors for distinguishing various aspects of a pedigree. Layout includes curved as well as straight lines.

33 Claims, 10 Drawing Sheets

US 6,932,024 B2

COMPACT PEDIGREES SHOWING HERITABLE TRAITS FOR MANY INDIVIDUALS

BACKGROUND

The present invention relates to studies of inherited characteristics in biological organisms, and more particularly concerns pedigrees of large populations of animals or plants.

Research into diseases, drugs, and genetic mechanisms in general frequently employ pedigrees of sexually reproducing organisms for tracing the inheritance of specific characteristics through a number of generations. The right kind of pedigree display can cause relevant inheritance patterns to become readily apparent, while other pedigree configurations obscure these patterns in the details of the pedigree format.

Many applications, such as breeding, genetic selection, and gene mapping, involve large populations of animals or plants, hundreds or thousands of individuals, and matings resulting in many offspring. Conventional pedigrees bury the relevant information so deeply in the overhead of the physical representation that the pedigree is not useful in extracting particular inheritance configurations of a particular trait or condition being studied.

FIG. 1 shows an example pedigree display 100 produced by the "Pedigree Visualizer" computer program, publicly available from Kent Ridge Digital Labs. Rectangles indicate males, and ovals females; a diamond indicates unknown sex. Horizontal connectors between males and females symbolize matings. Vertical lines drop to the next generation, where horizontal bars have vertical lines to symbols for offspring of a mating. The filled symbols represent those individuals that present an inherited characteristic of interest. Pedigree 100 can accommodate only a few hundred individuals in a display that remains small enough to be in view all at once. It does not easily accommodate multiple matings or inbreeding. Depicting backbreeding is practically impossible.

FIG. 2 depicts a pedigree display 200 produced by the "Lineage" program, publicly available from the Department of Animal Science, Cornell University. This program theoretically supports large displays having hundreds or thousands of individuals. However, the relevant data, represented in the tiny dots at the lower ends of the fanned lines, is practically invisible at the size it must be drawn. Although Lineage can represent multiple matings and inbreeding, these feature add significant clutter to an already cluttered display, and further obscure the pertinent data. Backbreeding remains difficult or impossible to display adequately.

SUMMARY OF THE INVENTION

The present invention produces pedigree displays that can accommodate large numbers of individuals over many generations in a compact form, while presenting relevant traits or characteristics at a size large enough to allow a user to see patterns or configurations of interest. All mating modes are easily integrated into the display.

The invention inputs records for individuals to be represented, including status of a characteristic, then combines record information for offspring having common parents and status into groups. Instead of presenting each individual separately, the invention generates a pattern for each group of individuals, and formats the patterns into a pedigree. A monitor or printer then displays the pedigree.

DRAWING

DESCRIPTION OF EMBODIMENTS

Figure 1:
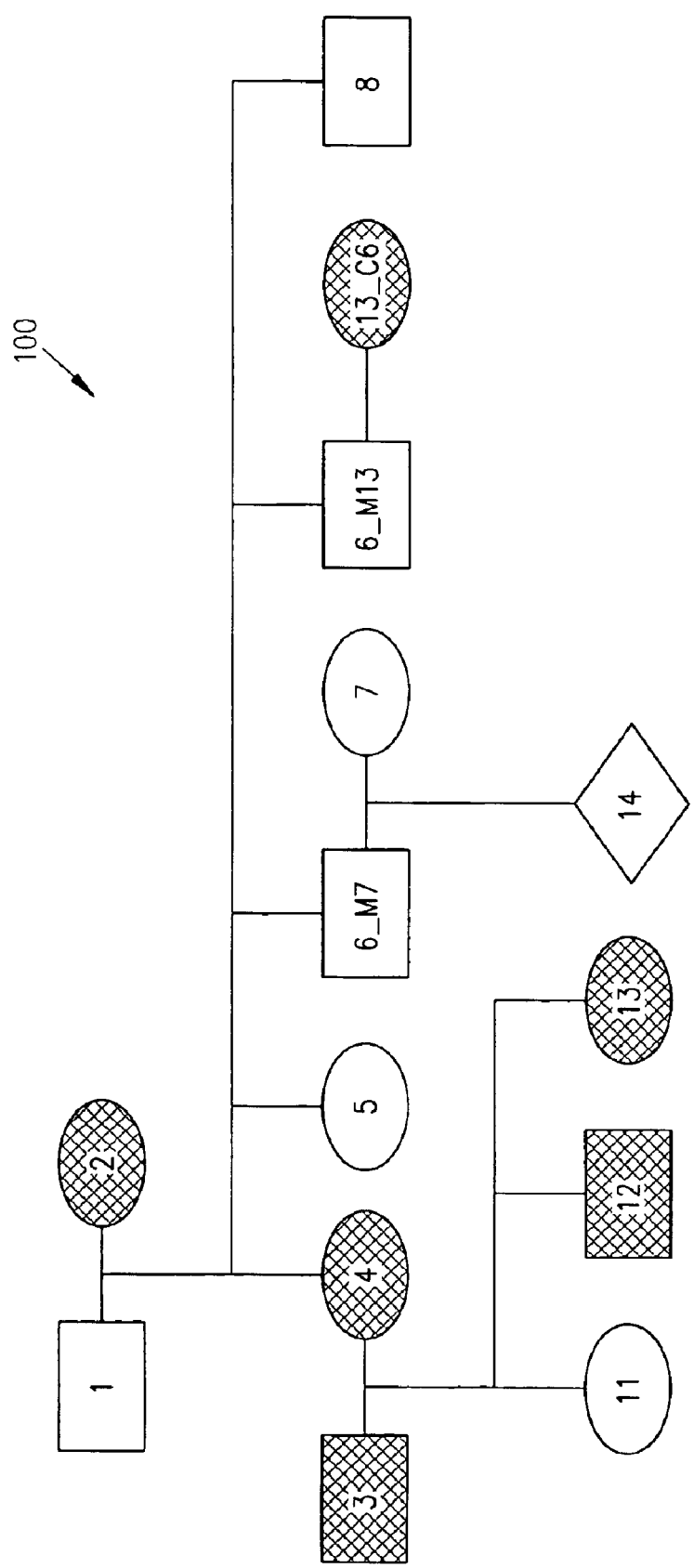
FIGS. 1 and 2 are displays of conventional pedigrees.

The following description and the drawing figures describe some specific embodiments of the invention sufficiently to enable those skilled in the art to practice the invention. Alternative embodiments may incorporate structural, logical, process, and other changes. Examples merely typify possible variations. Individual structures and functions are optional unless explicitly required, and the relative sequence of operations may vary. Portions and features of some embodiments may be included in or substituted for those of others. The scope of the invention encompasses the full ambit of the appended claims and all available equivalents.

Figure 3:
FIG. 3 shows input records for a pedigree according to the invention.

FIG. 3 shows a partial set of data records 300 for constructing a pedigree according to the invention. Each record such as 310 contains data for an individual. Field 301 employs a simple numeric code for this purpose. Any other representation that uniquely identifies an individual in the data records 300 will serve as well. In database terms, field 301 is a primary key. Fields 302 and 303 contain data representing the parents of the individual in field 301. Again, any code or representation that identifies these individuals is acceptable. Because the same individuals may appear in fields 301 as in 302 and 303, the codes for these fields should be compatible or interconvertible.

Field 304 indicates the sex of the individual in field 301 of the same record, since many of the characteristics of interest are sex-linked. Here again, the particular code for representing sex in field 304 is arbitrary. In some cases, sex is not significant and field 304 could be omitted. Field 305 contains a code having values for different conditions of a heritable trait of interest. For example, a cancer study might wish to trace the inheritance of a particular type of tumor through several generations. In this case, field 305 may contain a value, e.g., "1" to indicate that the individual identified in field 301 has a tumor of this type, and another value, e.g., "0", indicates the absence of a tumor. A record 310 might contain other fields, including more fields such as 305 for recording codes pertaining to additional characteristics of the individual identified in field 301. Fields 304 and 305 are termed condition fields, because they express the conditions or traits of interest concerning the individual identified in field 301 of the same record.

Figure 4:
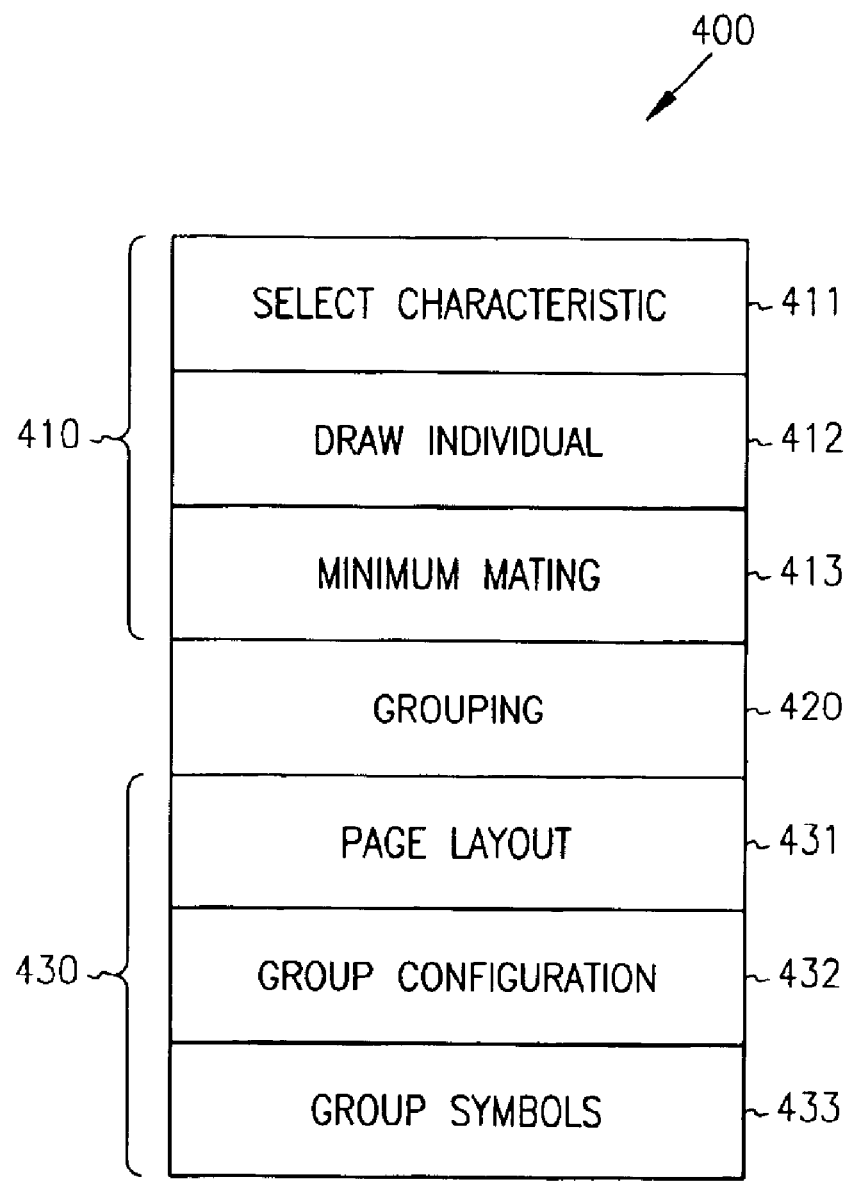
FIG. 4 is a list of parameters for controlling features of a pedigree display.

FIG. 4 lists some examples of optional parameters 400 for controlling a pedigree display.

If only some of the traits in multiple fields 305 are of interest in a pedigree, a user may input a parameter 411 to select one or more of the trait fields 305 for inclusion in a pedigree. Other data-selection controls 410 include parameter 412 to draw the subpedigree of only a particular individual identified in records 300. A user can choose to include siblings, ancestors, and/or descendants of the specified individual. Parameter 413 selects only those matings producing more than a certain number of offspring.

Data grouping parameters 420 specify how the mating data is to be summarized or grouped, as described below. In this context, a "mating" may include all offspring from a particular sire and dam, and not just a single litter. Matings between one sire and two different dams, or vice versa, are different matings, however.

Formatting parameters 430 designate details of the display. For example, page parameter 431 specifies page width, height, and other dimensions. Parameter 432 selects one of several configurations for displaying individual matings, as described below. Parameter 433 selects one of several symbol and color options for a pedigree display. Other possibilities for formatting options may include whether or not to align each generation in a horizontal row, although aligning is generally more informative. A visual feature, such as size or color, of the nodes representing individuals may be modified to indicate the genetic impact of that individual on the population; for example, a visually larger node might represent an individual having many offspring that also have many offspring, and thus a large impact. A visual feature such as size, color, or shading of a node may vary depending upon the degree to which the individual expresses a trait of interest; for example, an individual having higher milk production—or weight, etc.—might be more heavily shaded than one having a lower value of this trait. A visual feature of a group symbol may indicate the number of offspring in a group; for example, a group having more individuals might be larger than one having fewer. If parameter 412 specifies a particular individual, the pedigree of that individual may have a distinctive visual feature; rather than omitting other individuals from the pedigree, the pedigree might include all the individuals, but show the subpedigree of the particular individual in a different color, for example.

Figure 5:
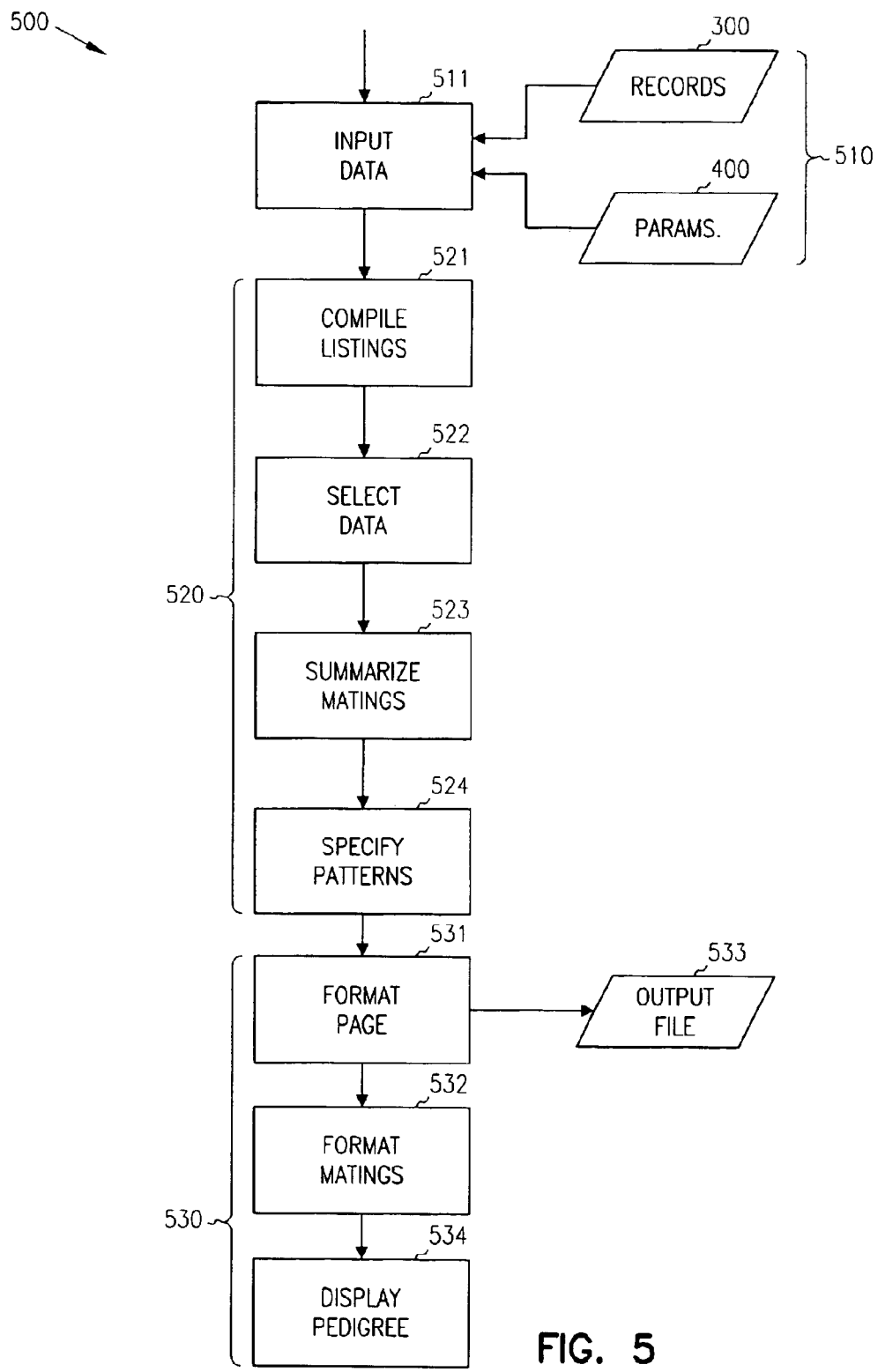
FIG. 5 shows a method for producing a pedigree display.

FIG. 5 is a flowchart of one method 500, called "Pedigraph," for producing a pedigree according to the invention. Blocks 510 input data. Block 511 receives data records 300 from a user or another program, and block 412 receives parameters 400.

Blocks 520 assemble the input records 300. Block 521 creates a listing of all individuals and matings from the input data records. Data validation may be performed at this point, such as checking for duplicate primary keys in field 301, and, where field 304 is blank, determining the individual's sex if possible. Block 522 marks those matings to be included in the pedigree, from parameters 410. Matings may be deleted if, for example, they produce too few offspring, or if they do not involve an individual specified in parameter 412. If the parameter specifies ancestors, then the selected individuals's ancestors are marked for inclusion; if siblings are included, then the individual's siblings and their offspring are marked.

Block 523 summarizes data for each mating to be included in the pedigree, according to the data in condition fields 304 and 305. For the example in FIG. 3, block 523 calculates the number of affected male offspring, affected female offspring, unaffected male offspring, and unaffected female offspring in each mating. That is, the two conditions, male/female and affected/unaffected, produce four groups for a mating, and each group is tagged with the number of offspring in that group. The condition or combination of conditions that define each group (such as "male, affected") is called a "category" herein.

Other ways of grouping the data are possible. For example, a single field 305 might contain a code expressing to what degree a trait affects the individual, and a parameter 420 might specify a division into six groups, having the categories:

male, unaffected;
male, slightly affected;
male, heavily affected;
female, unaffected;
female, slightly affected;
female, heavily affected.

As another example, some elemental combinations can be combined. For example, multiple fields 305 expressing two independent conditions having eight possible elemental combinations can be divided into six groups by a parameter 420:

male, unaffected by either trait;
male, affected by only one trait,
male, affected by both traits;
female, unaffected by either trait;
female, affected by only one trait;
female, affected by both traits.

Many other ways of grouping the offspring data from a mating are possible. Also, some applications may desire to tag each mating group with a designation other than a raw number of siblings in the groups. For example, symbols or other designations associated with a group may indicate that the number of affected male or female offspring is less than or greater than would be predicted by Mendelian inheritance. Other possible options for grouping offspring from a mating include grouping by genotype (the same genetic constitution) instead of by phenotype (status as to a particular trait). Individuals may be grouped by one parent instead of by both; for instance, all individuals having the same sire might be placed together in a group.

Block 524 manipulates some of the formatting parameters 430 to designate specific patterns to represent the groups in a pedigree display. The publicly available Dot program used in this example has a language for specifying graphs, nodes, and edges, which map easily into the terminology employed herein. For example, Pedigraph specifies a node line such as 612, FIG. 6, to Dot in the form "NODE_NAME [OPTIONS]," and specifies an edge line such as 611 in the form "NODE_NAME_1"->"NODE_NAME_2" [OPTIONS]." The following partial example of a Dot input file produces the example node 1000, FIG. 10.

```
digraph ped1 {
node[fontname="Arial"]
label="";
ranksep=1.1;
"Sire" [color=green, shape=box];
"Dam" [color=green, shape=circle,style=filled,fillcolor=lightgrey];
"DamxSire" [label="",height=.01,width=.01];
"Dam" -> "DamxSire" [dir=none,color=black];
"Sire" -> "DamxSire" [dir=none,color=black];
"DamxSireoffspring" [shape=record,label="3|1|3|1|",height=0.2,
  width=0.4];
"DamxSire" -> "DamxSireoffspring" [dir=none,color=black];
}
```

Blocks 530 assemble a pedigree as a construct known in mathematics as an "acyclic directed graph" having a set of "nodes" or "vertices" each containing information from the matings and groups identified above, and "edges" or "arcs" connecting the nodes. In one embodiment, blocks 530 are implemented by the program called "Dot," which draws hierarchical layouts of acyclic graphs. Dot is a part of a publicly available open-source graph-drawing package called "GraphViz," developed by American Telephone and Telegraph Corp. The data input to blocks 530 in one embodiment specifies two types of nodes. Because every junction of edges is a node in a graph, both the collection symbols representing matings and the offspring groups (see FIG. 6) are sent to blocks 530 as "nodes" in the graph; however, blocks 520 automatically specify the two types to have differing appearances.

Block 531 formats a pedigree for page sizes, titles, and so forth from formatting parameters 430. Block 532 formats each mating as a node having lines representing the graph edges from the parent individuals, the sire and dam, involved in the mating to a dot or other collection symbol representing the node, and one or more lines or other representations of edges to nodes representing the offspring or descendants that issue from the mating, as described in greater detail below. Although other methods are possible, a four-pass procedure can be employed to lay out the graph as a physical display. Using graph-theoretic terminology, the first pass finds an optimal rank assignment for each node, using a conventional network simplex algorithm. The second pass sets the order of edges within ranks; a heuristic incorporating a weight function and local transpositions reduces the number of line crossings in the physical layout. The third pass constructs and ranks an auxiliary graph to determine visually favorable node coordinates in the display. The fourth pass constructs splines to represent the edges of the graph as curved or straight lines.

Although any output format is usable for the layout of the pedigree graph, one embodiment can produce the pedigree as an output file 533 from block 532 in the PostScript® page-description language. ("PostScript" is a registered trademark of Adobe Systems Inc.) Block 534 displays the resulting pedigree on a printer from file 533, on a graphic display, or by any other convenient modality.

Figure 2:
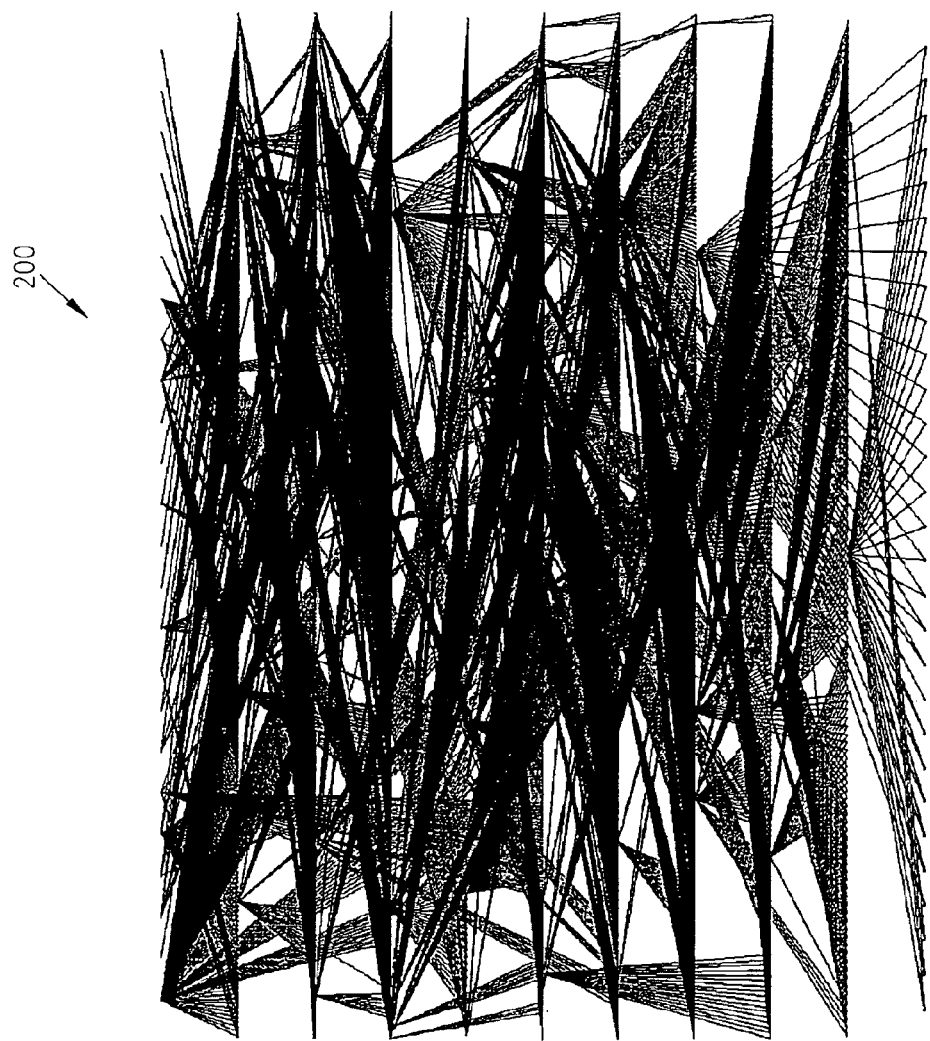
Figure 6:
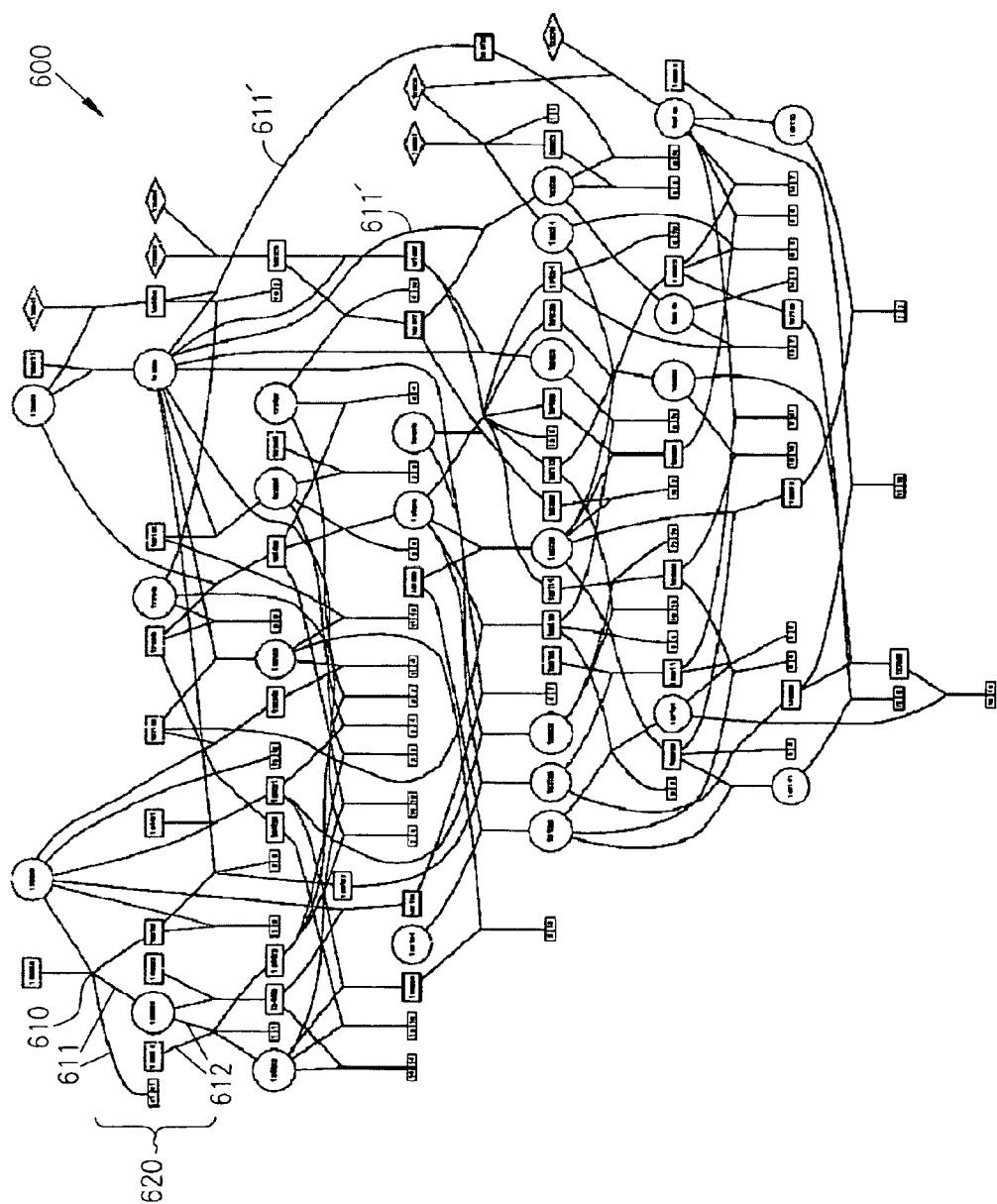
FIG. 6 is a display of a pedigree according to the invention.

FIG. 6 is an example of a pedigree display 600 produced by method 500. For comparison purposes, pedigree 600 includes the same individuals as does conventional pedigree 200, FIG. 2. That is, pedigrees 200 and 600 were produced from the same set of input records 300.

Pedigree 600 demonstrates a number of advantageous features. In each mating or node such as 601, the position of the collection symbol 610 is not restricted as are similar features indicating matings in most conventional pedigrees. Dot symbol 610 produced by block 532 conveniently locates below and near the parent having the nearest generation, but it can also be placed to reduce total line length, or according to any other criterion. Group symbols such as 620, further described below, have shapes, colors, and/or other prominent visible properties that indicate their respective categories, allowing an observer's eye to trace quickly the inheritance of one or more traits. Lines such as 611 from the collection symbols to the group symbols, and lines 612 from the parents to the collection symbols, may be any length, and can be curved as well as straight. This allows the group symbols to align easily into horizontal rows for each generation, even for multiple breedings, inbreedings, and backbreedings.

A major factor that facilitates ease of understanding is the grouping of multiple individuals into a single group symbol 620. The group symbol may contain or be otherwise associated with a numeral or other code relating to the number of individuals in the group. Because a single group symbol 620 can represent multiple individuals, multiple lines 612 from a single group symbol may represent parentage by different individuals as well as multiple matings of the same individual. However, all members of the group are in the same category. Therefore, this loss of detail, which allows significant simplification of the pedigree presentation, is not of consequence. If an individual in a group is involved in a mating to be included in a pedigree, the invention can draw an extra node to represent that individual, so that grouping individuals does not necessarily lose any detail.

Figure 7:
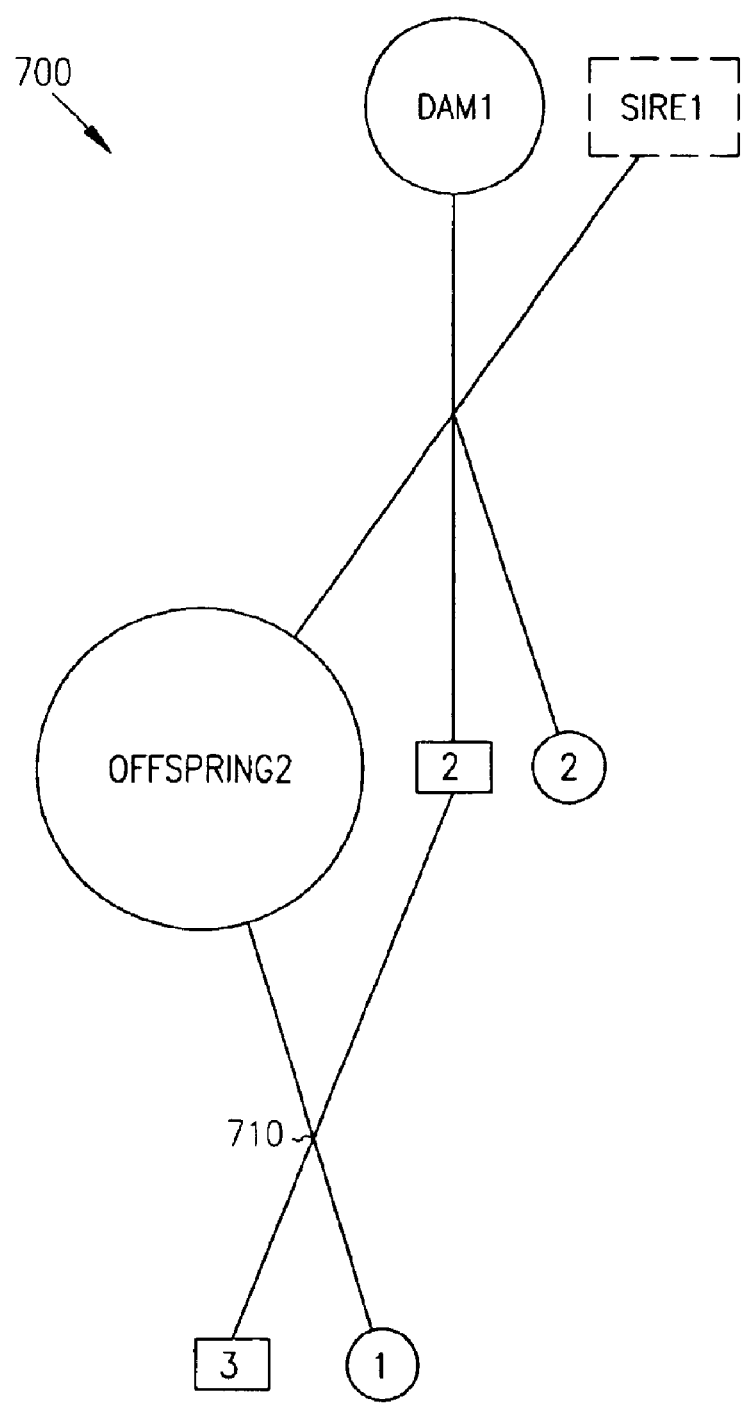
FIGS. 7 and 8 are displays of partial pedigrees at an expanded scale.
Figure 8:
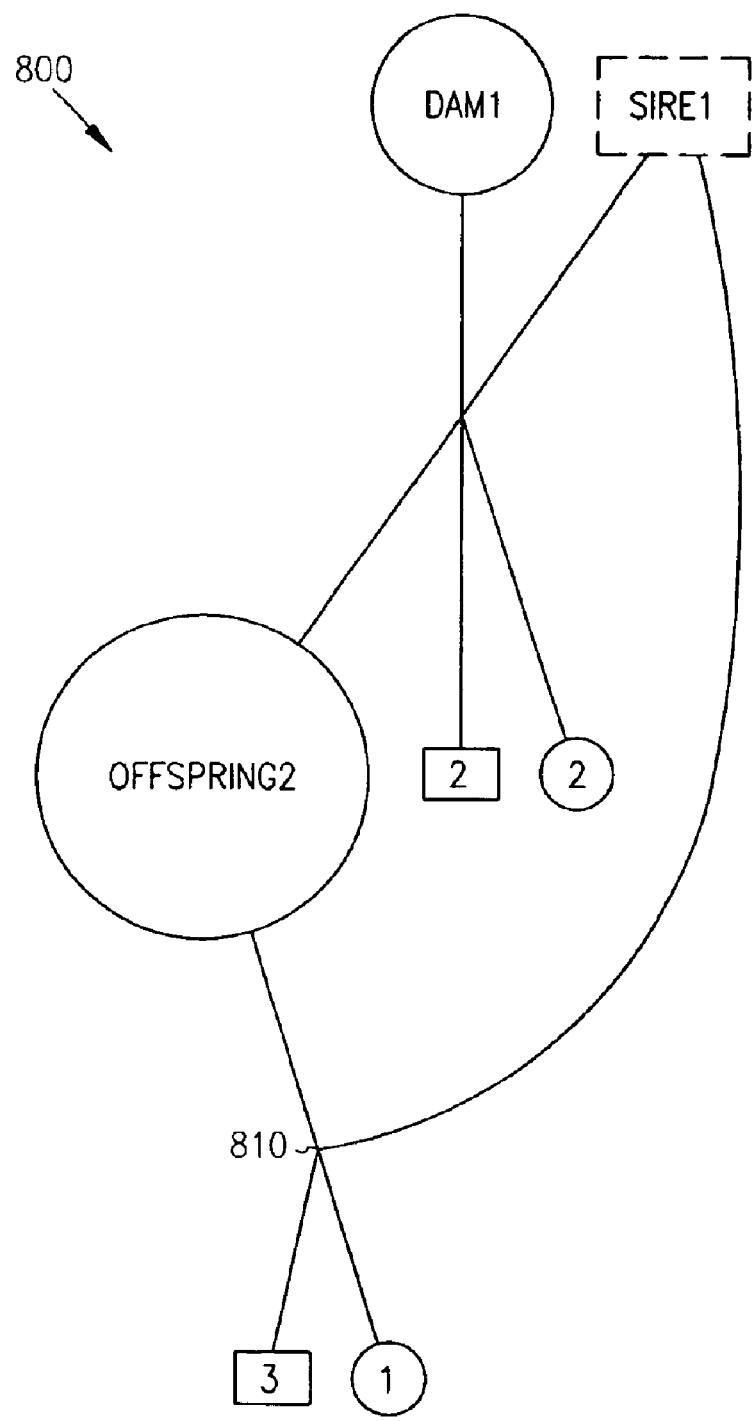

Another aspect of the invention that simplifies pedigrees is the use of curved lines 611 between collection symbols 610 and individuals. Examples of curved lines are indicated at 611'. The previously mentioned Dot program in the GraphViz package can produce such lines as splines and can automatically lay them out to avoid other objects in a graph. Curved lines have special advantages in large, complex pedigrees, for showing inbreeding and intergenerational matings. FIG. 7 shows a partial pedigree 700 at a larger scale that illustrates an inbred mating 710. FIG. 8 shows a partial pedigree 800 at a larger scale that illustrates intergeneration backbreeding at 810.

A further aspect for simplifying a pedigree 600 is the use of color and other visual features to indicate various characteristics. In human perception, color acts as a further dimension in explicating data patterns. Although the colors cannot be represented in FIG. 6, unaffected individuals can be shown as, for instance, green rectangles (males) and circles (females), while affected individuals are shown in a different color, such as red rectangles and circles. Visually tracing the colors through a sequence of matings permits an observer to grasp inheritance patterns more easily. Other visual devices may also distinguish different traits or characteristics, such as shaded and unshaded or larger and smaller sizes for symbols indicating affected and unaffected individuals.

Figure 9:
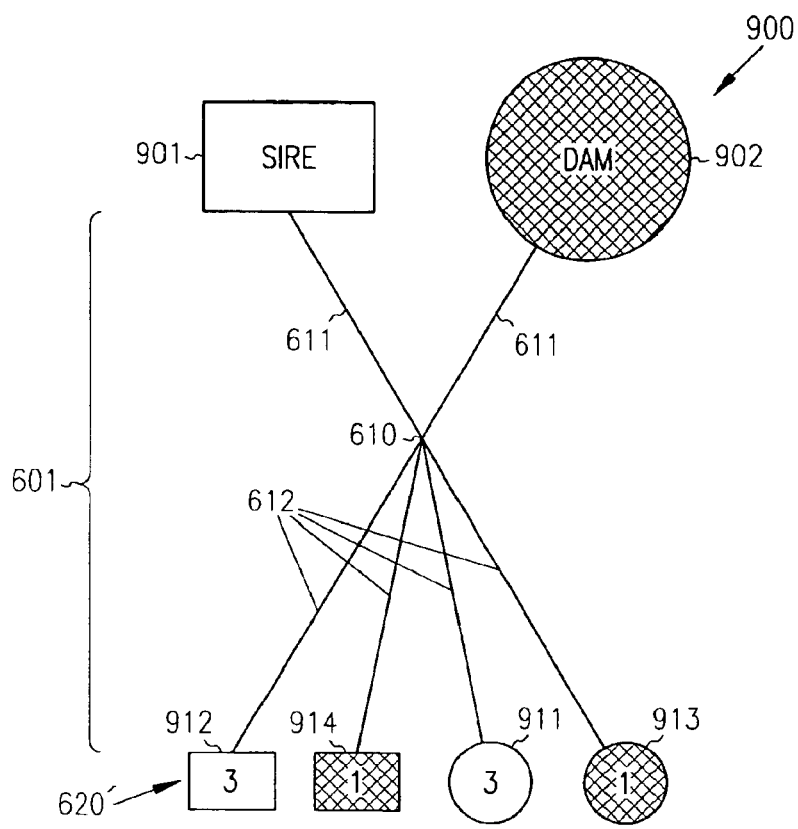
FIGS. 9 and 10 are displays of corresponding subsets of pedigree mating nodes at an expanded scale.
Figure 10:
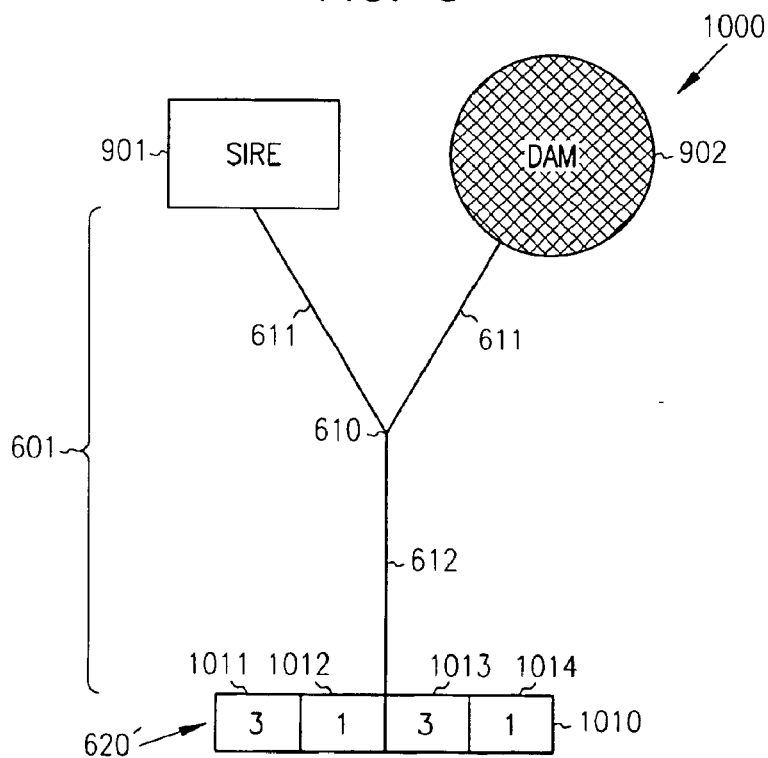

FIGS. 9 and 10 exemplify patterns for a single node 900 or 1000 of pedigree 600, shown here as a mating between a sire from a group of unaffected males, represented as an open rectangle 901, and a dam from a group of affected females, represented as a shaded oval 902. That is, the visible properties employed are rectangle or oval shapes to indicate sex, and open or shaded fills to indicate the value of a single binary condition field 305, FIG. 3. Here again, the shape may be colored green for unaffected status, and red for affected status.

In FIG. 9, the offspring of mating 900, in groups 620', use the same patterns. Open circle 911 signifies the category "unaffected female." It carries a numeral "3" to indicate that this group includes three individuals. Open rectangle 912 signifies a group having the category "unaffected males." The numeral in symbol 912 also shows three individuals in this group. The filled circle 913 and filled rectangle 914 signify "affected female" and "affected male" categories, respectively. The numerals in symbols 913 and 914 indicate one individual from the mating in each of these two groups. Group symbols 911–914 are separated from each other, and have separate lines 612 from collection point 610.

In FIG. 10, groups 620' are represented by a unitary symbol or block 1010 representing all the groups issuing from the mating, and having only a single line 612 from the collection point 610. The visual property that differentiates the groups in this case is the position of the numerals indicating the size of each category. Here, the numeral designated as 1011 signifies three individuals in the "unaffected female" category. Numeral 1012 signifies one offspring in the "affected female" category. Numerals 1013 and 1014 signify three unaffected males and one affected male.

Figure 11:
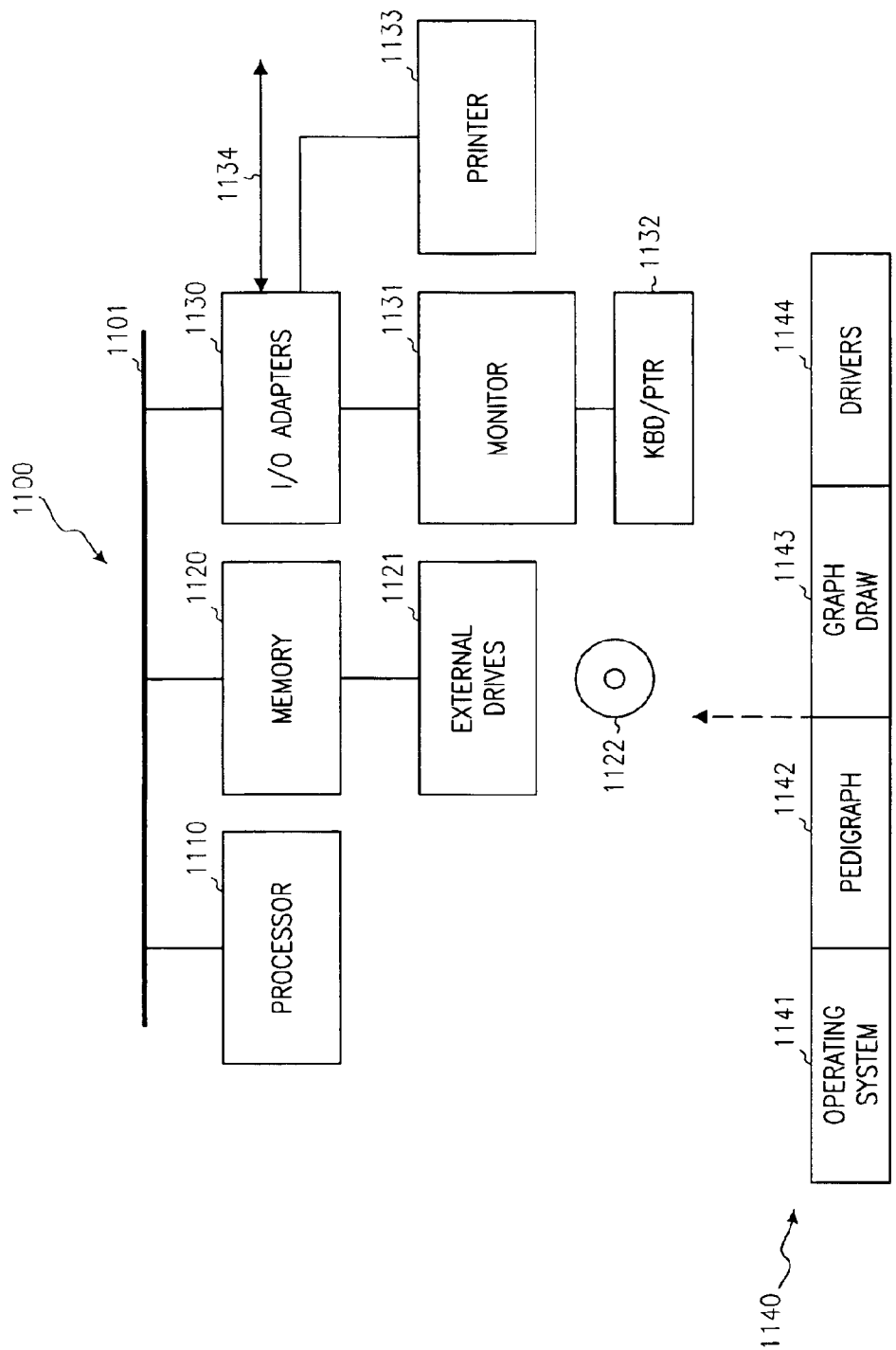
FIG. 11 is a block diagram of a system for carrying out the invention.

FIG. 11 shows an example of a system 1100 for hosting the invention. Bus 1101 interconnects a processor 1110, a memory system 1120, and input/output adapters 1130. Memory 1120 may be hierarchical, including cache, RAM, ROM, and one or more external drives such as 1121. These drives may include removable media such as disk 1122. Input/output units such as a display monitor 1131, a keyboard/pointer-device 1132 for entering input data 300 and parameters 400, and for displaying pedigrees 600. A printer 1133 for printing hard copies of pedigrees may also connect to adapters 1130. System 1130 may also include a connection 1134 to an external network, such as a LAN or the Internet, for data, parameters, and pedigree files.

Software 1140 may include an operating system 1141, a number of application programs 1142–1143, and drivers 1144 for I/O equipment 1130–1134. Application programs include a Pedigraph program constructed according to the invention, and a graph-drawing module such as the Dot program described earlier. The graph-drawing module may alternatively be included within the Pedigraph program, if desired. Drivers 1144 may include conventional PostScript® or other modules for printing pedigrees according to the invention. The dashed arrow indicates that the software may reside in memory system 1120, including removable media such as disk 1122. Software may also be communicated on connection 1134 to and from a network.

What is claimed is:

1. A method for producing in a data-processing system a pedigree of matings for a set of individuals, the method comprising:
   inputting records for the set of individuals, each record including data identifying a certain individual of the set of individuals, data identifying parents of the certain individual, and data indicating a status of the certain individual with respect to at least one heritable trait;
   for each of the matings, grouping the records into a plurality of groups, each group containing those individuals having common parents and having the same status with respect to the trait;
   formatting each group in one of the matings as a group node connected by one or more edges to any other groups in that mating and to a mating node representing that mating;
   repeating the above operation for others of the matings;
   producing a visual representation of the pedigree.

2. The method of claim 1 where the group nodes for individuals having different status values have different visual features.

3. The method of claim 2 where one of the visual features is color.

4. The method of claim 1 where the edges are lines.

5. The method of claim 4 where some of the edges are curved lines.

6. The method of claim 1 where the group nodes are symbol shapes.

7. The method of claim 6 where at least some of the symbol shapes indicate the number of individuals in the corresponding group.

8. The method of claim 7 where the some of the shapes include a numeral indicating the number of individuals in the corresponding group.

9. The method of claim 7 where the some of the shapes have a visual feature indicating the number of individuals in the corresponding group.

10. The method of claim 6 where the shapes for the groups in at least one mating are combined in a single block.

11. The method of claim 10 where the edges for the groups in the at least one mating are represented as a single line to the block.

12. The method of claim 1 where the mating nodes are dots.

13. The method of claim 1 where a subpedigree of a designated individual has a visual feature distinguishing the subpedigree from a remainder of the pedigree.

14. The method of claim 1 further comprising selecting only a portion of the pedigree for formatting and the visual representation.

15. The method of claim 14 where matings producing more than a certain number of offspring are selected.

16. The method of claim 14 where a subpedigree of a certain individual is selected.

17. The method of claim 1 where each record includes data indicating the sex of the individual.

18. The method of claim 17 where each group contains those individuals having common parents, having common sex, and having common status with respect to the trait.

19. The method of claim 18 where the group nodes for individuals having one sex have a different visual feature from the group nodes having the other sex.

20. The method of claim 1 where producing a visual representation of the pedigree comprises constructing a file containing data for displaying the pedigree.

21. The method of claim 1 where producing a visual representation of the pedigree comprises displaying the pedigree on a monitor.

22. The method of claim 1 where producing a visual representation of the pedigree comprises printing the pedigree on a printer.

23. A medium bearing machine-readable instructions for carrying out the method of claim 1.

24. A data-processing system for producing a pedigree of matings for a set of individuals, the system comprising:
   an input device for receiving records for the set of individuals, each record including data identifying a certain individual of the set of individuals, data identifying of the certain individual parents, and data indicating a status of the certain individual with respect to at least one heritable trait;
   a processor for grouping the records into a plurality of groups for each of the matings each group containing those individuals having common parents and having common status with respect to the trait, and for formatting each group in the matings as a group node connected by one or more edges to any other groups in mating and to a mating node representing the each mating;
   an output device for displaying a visual representation of the pedigree.

25. The system of claim 24 where the group nodes for individuals having different status values have different visual features.

26. The system of claim 25 where some of the edges are curved lines.

27. The system of claim 24 where the groups in at least one mating are combined in a single visual representation.

28. The system of claim 24 further comprising selecting only a portion of the pedigree for formatting and the visual representation.

29. The system of claim 24 where the output device is a monitor.

30. The system of claim 24 where the output device is a printer.

31. The system of claim 24 further comprising a storage system for storing instructions and data for carrying out the functions of the processor.

32. The system of claim 31 where the storage system includes a drive having a medium for storing instructions and data for carrying out the functions of the processor.

33. The system of claim 32 where the medium further includes instructions for controlling the output device for displaying the pedigree.

* * * * *

UNITED STATES PATENT AND TRADEMARK OFFICE
CERTIFICATE OF CORRECTION

PATENT NO. : 6,932,024 B2
DATED : August 23, 2005
INVENTOR(S) : Da et al.

It is certified that error appears in the above-identified patent and that said Letters Patent is hereby corrected as shown below:

<u>Column 8,</u>
Line 41, delete "of the certain individual parents," and insert -- parents of the certain individual, --, therefor.
Line 45, after "matings" insert -- , --.

Signed and Sealed this

Twenty-second Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,932,024 B2 Page 1 of 1
APPLICATION NO. : 10/339865
DATED : August 23, 2005
INVENTOR(S) : Yang Da, John R. Garbe It is certified that error appears in the above-identified patent and that said Letters Patent is hereby corrected as shown below:

On Title 1, Item (73) Assignee: delete "Cargill, Incorporated, Wayzata, MN (US)" and insert -- Regents of the University of Minnesota, Minneapolis, MN (US) --.

Signed and Sealed this

Twenty-eighth Day of November, 2006

JON W. DUDAS
*Director of the United States Patent and Trademark Office*